US00PP09509P

United States Patent [19]

Angus et al.

[11] Patent Number: Plant 9,509

[45] Date of Patent: Apr. 16, 1996

[54] *CHAMELAUCIUM UNCINATUM*—'CASCADE BROOK'

[75] Inventors: Timothy P. Angus, Faulconbridge; Nicholas F. Derera, Winston Hills, both of Australia

[73] Assignee: Newports Nurseries, Australia

[21] Appl. No.: 405,211

[22] Filed: Mar. 16, 1995

[51] Int. Cl.$^6$ ..... A01H 5/00

[52] U.S. Cl. ..... Plt./54.1

[58] Field of Search ..... Plt./54.1

*Primary Examiner*—James R. Feyrer

*Attorney, Agent, or Firm*—Christie, Parker & Hale

[57] ABSTRACT

A new and distinct variety of *Chamelaucium uncinatum* plant, named 'Cascade Brook', particularly charaterized by having an erect plant with numerous secondary stems which gracefully weep. Larger than normal flowers occur in summer and winter, with petals in a range of appealing, light to medium purple shades, and having dark purple nectaries.

2 Drawing Sheets

BACKGROUND INFORMATION

This invention relates to a new and distinct variety of *Chamelaucium uncinatum* which is referred to herein as the new variety "Cascade Brook". "Cascade Brook" was bred by breeders T P Angus and N F Derera, both of 244 Singles Ridge Road, Winmalee, New South Wales, 2777, Australia.

"Cascade Brook" resulted from a controlled pollination carried out on 10 March 1988 between *Chamelaucium uncinatum* variety GW23 (seed parent) by *Chamelaucium uncinatum* variety GW8 (pollen parent). "Cascade Brook" was selected in March 1991 on the basis of flowering time, petal colour, nectary colour, flower size and plant habit. "Cascade Brook" was shown to be stable through two vegetatively propagated generations. The breeding and subsequent characterization of "Cascade Brook" were carried out at Winmalee, New South Wales, Australia.

"Cascade Brook" is most notable for its predominance of mature petal colour R.H.S. No 75A, its large flower diameter (mean greater than 18 millimeters), its biannual flowering habit (winter and summer) and its predominant mature nectary colour of R.H.S. No 187C.

"Cascade Brook" has been vegetatively propagated by means of striking plant cuttings at the above-noted location, at Winmalee, New South Wales, Australia. Examination of various "Cascade Brook" plants has confirmed that the combination of characteristics described herein are firmly fixed throughout successive generations.

DESCRIPTION OF THE DRAWINGS

"Cascade Brook" is illustrated by the accompanying photograhic drawings.

DESCRIPTION OF THE NEW VARIETY

Figure 1:
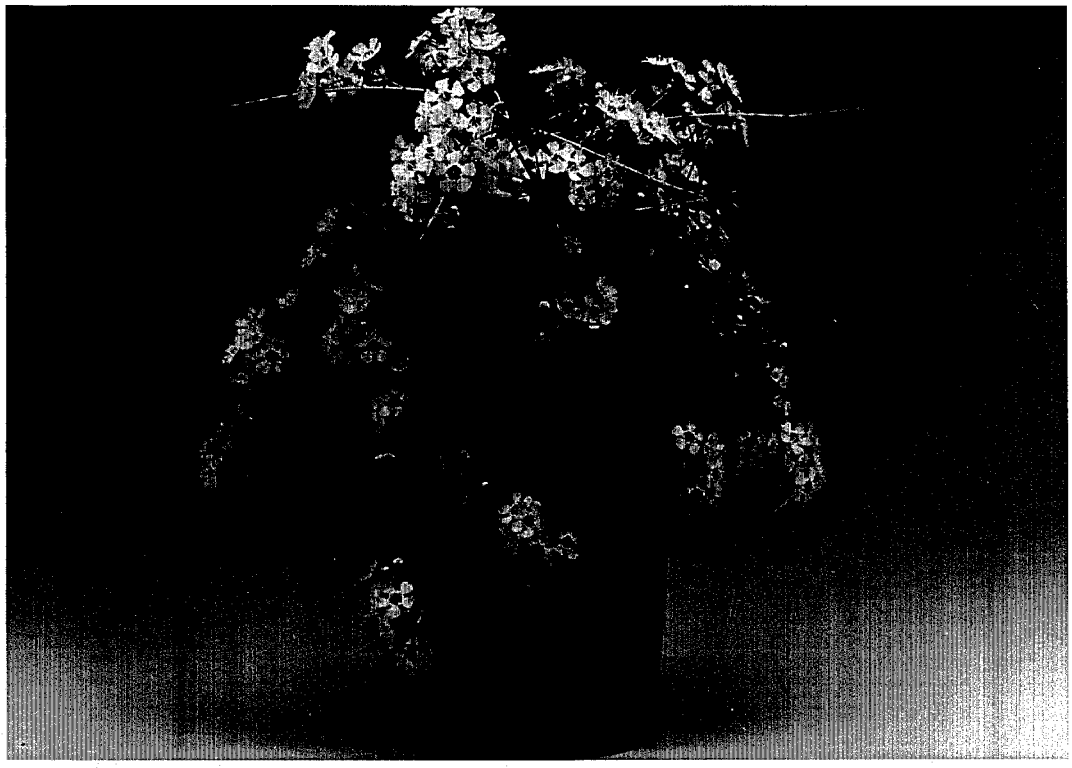
FIG. 1: Is a photographic print in full colour showing a single potted specimen of "Cascade Brook" which was planted in approximately January 1994. The photograph was taken in June 1994 and the plant is approximately 25 centimeters high×35 centimeters wide.
Figure 2:
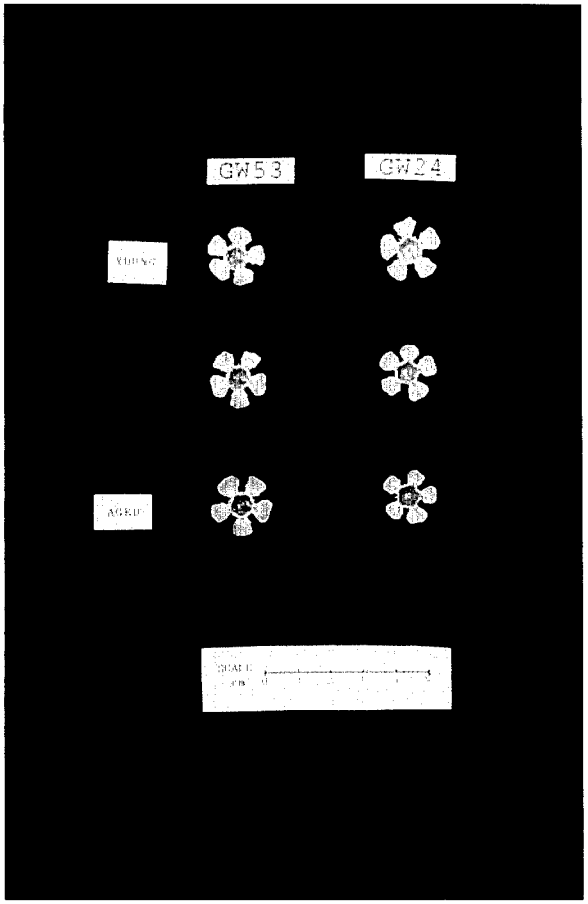
FIG. 2: Is a photographic print in full colour which compares flowers "Cascade Brook" (signified "GW53"), with comparative *Chamelaucium uncinatum* variety "Pink" (GW24). The figure shows petal coloration from young flower to aged flower.

The following is a detailed description of the "Cascade Brook" with colour designations according to the *Horticultural Colour Chart* issued by the British Colour Council in collaboration with The Royal Horticultural Society Copyright 1938. The observed traits have been repeatedly observed and are believed to be characteristic of "Cascade Brook" which, in combination, distinguish "Cascade Brook" as a new and distinct cultivar.

Locality: "Cascade Brook" was grown and observed at Newport Nurseries, Winmalee, New South Wales, Australia.

Propagation: By cutting.

Parentage: Controlled pollination of *Chamelaucium uncinatum* GW23 (seed parent) by *Chamelaucium uncinatum* GW8 (pollen parent).

Growth habit: Erect plant habit with cascading or weeping new growth, particularly when grown under conditions such as 25° C. to 30° C. day/15° C. to 18° C. night temperatures with high nutrition.

Shape: When grown in a glasshouse with weekly nutrient supply the plants develop a spreading semi-erect habit with new growth weeping/hanging down from the more erect firm older growth.

Size: When grown in 130 millimeter pots in a glasshouse with nutrients supplied weekly approximate dimension twelve months from rooted cutting are:

*Height.*—60 to 75 centimeters.

*Width.*—60 to 75 centimeters.

Line growth: High branching frequency on main stem and side branch. Medium to high branching frequency on side branches.

Foliage: Mature leaflets at branched node with length 40 to 55 centimeters; diameter of approximately 1 millimeter, opposite, linear, almost terete with spreading hooked apex, spreading to reflexed, and glabrous. Colour R.H.S. No 146A (yellow-green colour group).

Flowers: Flowering is biannual with flowering between December to March (summer flowering) and July to September (winter flowering). Characteristics of flowering are as follows:

*Summer flowering.*—Flower diameter: Mean about 18.4 millimeters. Mature petal colour: R.H.S. No 77C 84C. Mature nectary colour: R.H.S. No 183A 187 AB.

*Winter flowering.*—Flower diameter: Mean about 18.6 millimeters. Mature petal colour: R.H.S. No 75A. Mature nectary colour: 187C.

Flower size is large compared to other *Chamelaucium uncinatum.* The petal outline is notched and the petal margin is undulate. The predominate floral tube outline is conical.

In the northern hemisphere flowering results would generally be the reverse of that set out above. Summer flowering results would be observed between July to September and winter flowering results would be observed between December to March. Comparisons of summer and winter flowering based on twenty plants are set out in Table 1.

TABLE 1

CHARACTERISTICS OF *CHAMELAUCIUM UNCINATUM* CASCADE BROOK

| | CASCADE BROOK Summer Flowering | CASCADE BROOK Winter Flowering |
|---|---|---|
| PLANT HABIT | Cascading | Cascading |
| FLOWERING TIME (50% bud burst) | December/January/ February | August/ September |
| BUD COLOUR With Operculum | | |
| Colour | Red | Red |
| RHS No | 41A 42C | 41A 42C |
| Without Operculum | | |
| Colour | Purple | Purple |
| RHS No | 77BC | 77C |
| FLORAL TUBE, MID-REGION | | |
| Colour | Green or yellow green or red-purple | Yellow-green or red-purple |
| RHS No | 59B 143C 144A | 59B 144A |
| FLOWER DIAMETER (mm) | | |
| Mean | 18.6 | 20.8 |
| Range | 17.8–19.6 | 19.1–22.0 |
| PETAL | | |
| Outline | Obovate | Obovate |
| Immature colour | | |
| Colour | Purple | Purple |
| RHS No | 75C 77CD | 75A |
| Colour Development | Fast | Fast |
| Mid-mature colour (% to 15 days after bud burst) | | |
| Colour | Purple or violet | Purple or violet |
| RHS no | 75AB 84BC | 75AC 84C |
| Petal | | |
| Mature Colour (ca 20 days after bud burst) | | |
| Colour | Purple or violet | Purple |
| RHS No | 77C 84C | 75A |
| NECTARY | | |
| Immature colour | | |
| Colour | Green | Yellow-green |
| RHS No | 141C 143AC | 149B |
| Mature colour | | |
| Colour | Greyed-purple | Greyed-purple |
| RHS No | 183A 187AB | 187C |
| STAMINODIA | | |
| Outline | Narrow tri-angular (NT) | NT |
| Mature collar colour | | |
| Colour | White | White |
| RHS No | 155D | 155D |
| STYLE COLOUR | | |
| Immature colour | | |
| Colour | Red-purple or white | White |
| RHS No | 64D 70C 155D | 155D |

TABLE 1-continued

CHARACTERISTICS OF *CHAMELAUCIUM UNCINATUM* CASCADE BROOK

| | CASCADE BROOK Summer Flowering | CASCADE BROOK Winter Flowering |
|---|---|---|
| Mid-mature colour | | |
| Colour | Red-purple or white | White |
| RHS No | 64D 70C 155D | 155D |
| Mature colour | | |
| Colour | White | White |
| RHS No | 155D | 155D |
| CALYX LOBE | | |
| Mid-mature colour | | |
| Colour | Red-purple | Red-purple |
| RHS No | 62D 65C 73D | 65C 73D |
| Mature colour | | |
| Colour | Purple | Purple |
| RHS No | 76D | 76D |
| FLORAL TUBE | | |
| Outline | Conical | Conical |
| Fluting | Present | Present |
| Diameter (mm) | | |
| Mean | 8.45 | 9.2 |
| Range | 7.9–9.0 | 8.7–9.8 |
| Mid-point colour | | |
| Colour | Yellow-green or green | Yellow-green |
| RHS No | 143C 144BC 145A | 144C |
| FLOWER ARRANGEMENT | Broad distal (BD) | BD |
| FLOWER FRAGRANCE | Present | Present |

The characteristics of "Cascade Brook" were compared with the closest known *Chamelaucium uncinatum* variety "Pink". Observations were made during the winter of 1992 and summer of 1992/1993 from ten plants of each of "Cascade Brook" and "Pink". The plants were selected at random in June 1992 from twelve months old plants grown in a glasshouse at Winmalee, New South Wales, Australia. Results are set out in Table 2.

TABLE 2

DRAFT COMPARISON TABLE

| CHARACTER | "PINK" GW24 | CASCADE BROOK GW53 |
|---|---|---|
| FLOWERING TIME | Medium July to September | Early and medium January to March July to September |
| FLOWERING DIAMETER (MM) | | |
| Mean | 18.1 | 18.4 |
| Std deviation | 0.953 | 0.872 |
| No measured | 20 | 20 |
| PETAL COLOUR | | |
| Immature | 75 with margins of 155D | 75A with margins of 155D |
| Mature | 75A with margins of 155D | 75A with margins of 72C |

TABLE 2-continued

| DRAFT COMPARISON TABLE | | |
|---|---|---|
| CHARACTER | "PINK" GW24 | CASCADE BROOK GW53 |
| NECTARY COLOUR | | |
| Immature | 149B | 149B |
| Mature | 186B | 187C |
| FLOWER ARRANGEMENT | Broad distal | Broad distal |

We claim:

1. A new and distinct *Chamelaucium uncinatum* plant substantially as shown and described herein, distinguished principally from other varieties of its type by biannual flowering, petal colour, mature nectary colour and flower size.

* * * * *